United States Patent
Levorse, Jr. et al.

(10) Patent No.: US 7,511,001 B2
(45) Date of Patent: Mar. 31, 2009

(54) SUBSTITUTED CYCLOHEXYL PROPANAL COMPOUNDS AND THEIR USE IN PERFUME COMPOSITIONS

(75) Inventors: Anthony T. Levorse, Jr., Westfield, NJ (US); Brett D. Newirth, Sea Bright, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 101 days.

(21) Appl. No.: 11/831,243

(22) Filed: Jul. 31, 2007

(65) Prior Publication Data
US 2009/0036347 A1     Feb. 5, 2009

(51) Int. Cl.
*C11D 3/50* (2006.01)
(52) U.S. Cl. ............... 510/106; 512/22; 568/420
(58) Field of Classification Search ........... 510/106; 512/22; 568/420
See application file for complete search history.

(56) References Cited

U.S. PATENT DOCUMENTS

| 4,131,623 | A | 12/1978 | Meyers | |
|---|---|---|---|---|
| 2004/0102357 | A1* | 5/2004 | Smith et al. | 512/3 |
| 2005/0101783 | A1* | 5/2005 | Ito et al. | 546/329 |
| 2005/0233938 | A1* | 10/2005 | Delplancke et al. | 510/507 |

FOREIGN PATENT DOCUMENTS

| DE | 501627 | 7/1930 |
|---|---|---|
| JP | 48035065 | 10/1973 |
| JP | 9077712 | 3/1997 |
| WO | WO 2008/053148 A1 * | 5/2008 |

OTHER PUBLICATIONS

Gunther Ohloff et al. Nr. 127 Conformationally Controlled Odor Perception in 'Steroid-type' Scent Molecules. (1983) Helvetica Chimica ACTA 66(5) pp. 1343-1354.
Cyril Ollivier et al. B-Alkylcatecholboranes as a Source of Radicals for Efficient Conjugate Additions to Unsaturated Ketones and Aldehydes. (1999) Chemistry—A European Journal 5(5) pp. 1468-1473.
Bernd Giese et al. Tris(trimethylsilyl)silane As Mediator In Organic Synthesis Via Radicals. (1989) Tetrahedron Letters 30(681) pp. 681-684.
Roland Koster et al. Boron Compounds, XXXIX. Alkenoxy(diorganyl)boranes Substituted At The Alkenoxy Group From 2-Methylacrolein And Triorganylboranes. (1976) Justus Liebigs Annalen der Chemie 6 pp. 1116-1134.
Richard Lai et al. Hydroformylation Of Allylbenzene By Complexes Formed In Situ From Rhodium (1973) Sciences Chimiques 276(5) pp. 425-428.
Albert Irving Meyers et al. Syntheses Via Dihydro-1,3-oxazines. VII. A Simple Synthesis Of Unsymmetrical Ketones. (1969) Journal of the American Chemical Society 91(21) pp. 5887-5888.
Herbert C. Brown et al. Reaction Of Organoboranes With 2-Bromoacrolein. A Facile One-stage Synthesis Of Alpha-bromo Aldehydes. (1968) Journal of the American Chemical Society 90(15) pp. 4165-4166.
Philip Jones et al. Conjugate Michael Additions With Mixed Diorganozincs. (1998) Tetrahedron 54(8) pp. 1471-1490.
Philip Jones et al. Conjugate Michael-Additions With Mixed Diorganozincs. (1997) Perkin Transactions 1: Organic and Bio-Organic Chemistry 21 pp. 3117-3118.

* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention relates to substituted cyclohexyl propanal compounds and their use in enhancing fragrance formulations in perfumes, toilet waters, colognes, personal products, and the like.

16 Claims, No Drawings

SUBSTITUTED CYCLOHEXYL PROPANAL COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of a molecule can result in significant differences in the odor, notes, and characteristics of the molecule. These variations and the ongoing need to develop new fragrances allow perfumers and other persons to apply new chemicals in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to substituted cyclohexyl propanal compounds, represented by the general formula set forth below:

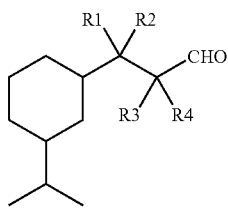

Formula I wherein $R_1$, $R_2$, $R_3$, and $R_4$ is independently hydrogen or methyl.

Another embodiment of the invention is a method for enhancing a perfume composition by incorporating an olfactory acceptable amount of the compounds provided above.

These and other embodiments of the present invention will be apparent by reading the following specification.

DETAILED DESCRIPTION OF THE INVENTION

In a preferred embodiment of the invention, the novel compounds of the present invention are represented by the following structures:

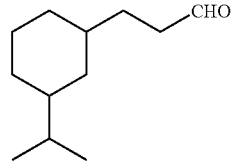

Structure I

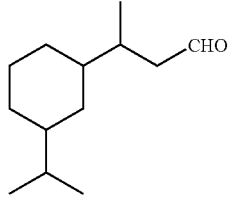

Structure II

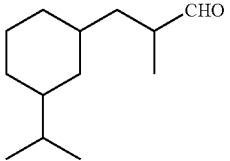

Structure III

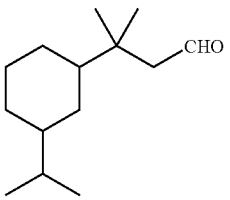

Structure IV

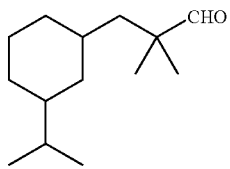

Structure V

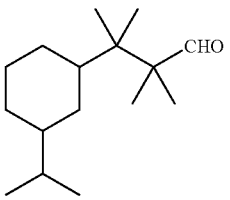

Structure VI

Those with the skill in the art will appreciate that the following compounds:

Structure I is beta-(3-isopropyl-cyclohexyl)-propionaldehyde;

Structure II is beta-(3-isopropyl-cyclohexyl)-butyraldehyde;

Structure III is beta-(3-isopropyl-cyclohexyl)-alpha-methyl-propionaldehyde;

Structure IV is beta-(3-isopropyl-cyclohexyl)-beta-methyl-butyraldehyde;

Structure V is beta-(3-isopropyl-cyclohexyl)-alpha,alpha-dimethyl-propionaldehyde; and Structure VI is beta-(3-isopropyl-cyclohexyl)-alpha,alpha,beta-trimethyl-butyraldehyde.

The compounds of the present invention may be prepared from the corresponding meta isopropyl-benzene aldehydes employing a three step reaction sequence. The aldehyde group is protected as a methyl acetal using orthoformate in methanol in the presence of catalytic acid. Reduction of the aromatic ring with hydrogen over a precious metal catalyst affords the cyclohexyl ring system. Deprotecting the masked aldehyde gives the desired meta substituted aldehydes. The reactions are illustrated by the following sequence:

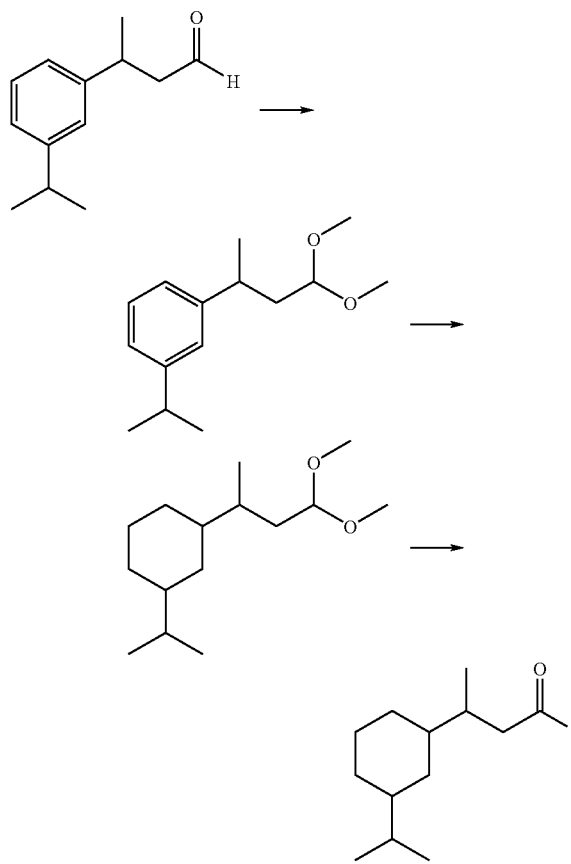

We have discovered that the compounds of the present invention have an orris character and an earthy fatty character that are well suited for use as a fragrance ingredient. In particular, Structure II possesses a complex odor character of orris, earthy, fatty, and powdery notes.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners, fabric care products such as but not limited to fabric softeners, dryer sheets and the like.

In these preparations, the compounds of the present invention can be used alone or in combination with other perfuming compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8, and more preferably from about 0.5 to about 5 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds, as parts per million (ppm) of the materials added to impart the desired fragrance. The compounds of the invention can range widely from 0.005 to about 10 ppm of the perfumed composition, and preferably from about 0.1 to about 5 ppm. Those with skill in the art will be able to employ the desired level of the compounds of the invention to provide the desired fragrance and intensity.

All U.S. patents and patent applications cited herein are incorporated by reference as if set forth herein in their entirety.

The following are provided as specific embodiments of the present invention. Other modifications of this invention will be readily apparent to those skilled in the art, without departing from the scope of this invention. Upon review of the foregoing, numerous adaptations, modifications and alterations will occur to the reviewer. These adaptations, modifications, and alterations will all be within the spirit of the invention. Accordingly, reference should be made to the appended claims in order to ascertain the scope of the present invention.

As used herein all percentages are weight percent. IFF is meant to be understood as International Flavors & Fragrances Inc., New York, N.Y., USA.

EXAMPLE I

Preparation of beta-(3-isopropyl-cyclohexyl)-butyraldehyde (Structure II)

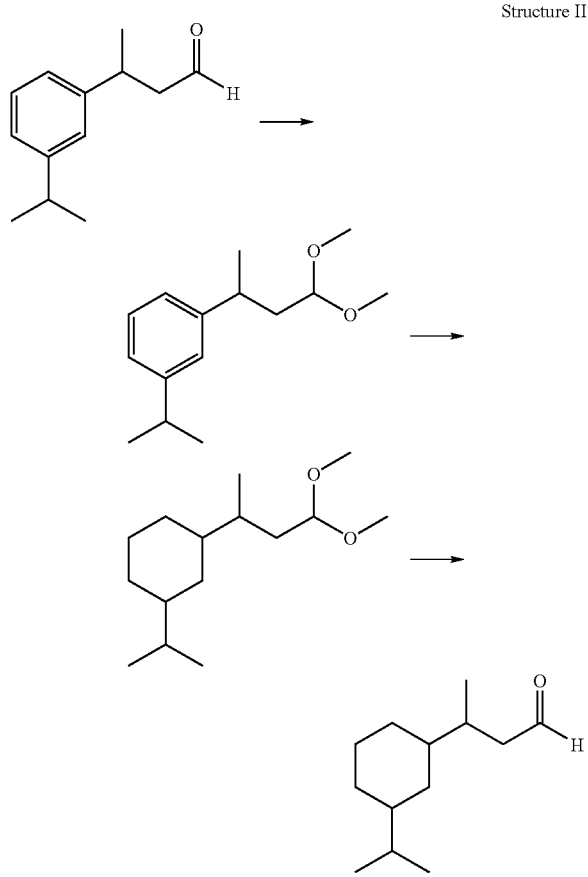

Structure II

Florhydral® (commercially available from Givaudan) 1579 g (8.3 mole), methanol 1 L and trimethylorthoformate 911 g (8.6 mole) were combined in a reaction flask and cooled to 0° C. In one portion 2 g (0.02 mole) 37% aqueous hydrochloric acid was added. The reaction exotherm was used to raise the reaction temperature to 20° C. The reaction mass was aged at room temperature for 1 hr then sodium methoxide solution was added (10 g of 25% NaOMe/MeOH). The reaction mass was heated to 90° C. during which lites and methanol were recovered using a Dean-Stark trap. The crude reaction mass was washed with brine (500 ml).

Distillation afforded 1745 g of 1-(3,3-dimethoxy-1-methylpropyl)-3-(1-methylethyl)-benzene.

Distilled 1-(3,3-dimethoxy-1-methylpropyl)-3-(1-methylethyl)-benzene 868 g (3.6 mole) and ruthenium on alumina 1 g were charged to an autoclave and placed under a hydrogen atmosphere. The autoclave was pressurized to 500 psi and heated to 130° C. The hydrogenation was aged for 8 hrs. The crude mass was removed from the autoclave and filtered through celite to remove the catalyst.

Crude filtered 1-(3,3-dimethoxy-1-methylpropyl)-3-(1-methylethyl)-cyclohexane 440 g, acetone 1L, water 200 ml and 37% aqueous hydrochloric acid 5 g were combined in a reaction flask and heated to reflux. The reaction was aged for 12 hrs then quenched with sodium acetate 8 g (0.1 mole). The aqueous layer was separated and the organic layer distilled.

Distillation afforded 210 g of beta-(3-isopropyl-cyclohexyl)-butyraldehyde.

Odor Character: Orris, Earthy, Fatty, and Powdery.

1HNMR: 0.66-0.77 ppm (m, 1H), 0.81-0.90 ppm (m, 7H), 0.91-0.95 ppm (m, 3H), 1.04-1.11 ppm (m, 1H), 1.14-1.26 ppm (m, 2H), 1.37-1.44 ppm (m, 2H), 1.59-1.68 ppm (m, 3H), 1.78-1.82 ppm (m, 1H), 1.95-2.02 ppm (m, 1H), 2.17-2.24 ppm (m, 1H), 2.41-2.49 ppm (m, 1H), 9.76 ppm (t, 1H, J=2.38 Hz).

EXAMPLE II

Fragrance formula: melon type.

| Fragrance Ingredient | Parts |
| --- | --- |
| Aldehyde AA | 1.50 |
| Aldehyde C16 | 35.00 |
| Allyl cyclohexyl propionate | 7.5 |
| Allyl heptenone | 12 |
| Amberttolide | 1.5 |
| Benzyl acetate | 35 |
| Benzyl propionate | 7.5 |
| Citronalva | 2.5 |
| Coumarin | 2.5 |
| Cyclaprop | 45 |
| Cyclobutanate | 30 |
| Gamma decalactone | 5 |
| Ethyl butyrate | 2.5 |
| Ethyl vanillin | 1.5 |
| Fructone | 125 |
| Geraniol 980 | 10 |
| Hedione | 30 |
| Heliotropine | 5 |
| cis-3-Hexenyl acetate | 1.5 |
| Hexyl cinnamic aldehyde | 30 |
| Beta ionone | 35 |
| Iso amyl butyrate | 2 |
| Linalool | 30 |
| Lyral | 45 |
| Melonal | 2 |
| Nerol | 10 |
| Oxyphenylon | 10 |
| Peach aldehyde | 250 |
| PEA | 125 |
| Styralyl acetate | 5 |
| Veltol | 20 |
| Vertenex | 45 |
| beta-(3-isopropyl-cyclohexyl)-butyraldehyde | 25 |

Evaluation of the above fragrance formula indicates that beta-(3-isopropyl-cyclohexyl)-butyraldehyde imparts a fresh character of melon.

EXAMPLE III

Fragrance formula: fresh green type.

| Fragrance ingredient | Parts |
| --- | --- |
| Aldehyde C-11 | 0.45 |
| Benzyl acetate | 1.50 |
| Cassis base | 0.75 |
| Cyclogalbaniff | 0.75 |
| beta-(3-isopropyl-cyclohexyl)-butyraldehyde | 3.0 |
| *Eucalyptus* oil | 1.05 |
| DPG | 26.92 |
| Galaxolide | 14.96 |
| Hedione | 22.44 |
| Hexenol b | 0.75 |
| Iso E Super | 5.98 |
| Lavender oil | 0.3 |

-continued

| Fragrance ingredient | Parts |
| --- | --- |
| Lemon oil | 4.49 |
| Lime oil | 2.99 |
| Limonene | 4.49 |
| Menthone | 0.45 |
| Methyl anthranilate | 0.75 |
| Nonadienal | 0.07 |
| Orange oil | 2.24 |
| Sanjinol | 1.5 |
| Santaliff | 0.3 |
| Undecavertol | 0.75 |
| Vanillin | 0.15 |
| verdox | 2.99 |

Evaluation of the above fragrance formula indicates that beta-(3-isopropyl-cyclohexyl)-butyraldehyde imparts the freshness of a green character.

What is claimed is:

1. A compound

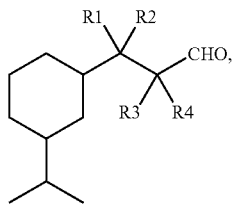

wherein $R_1$, $R_2$, $R_3$, and $R_4$ is independently hydrogen and methyl.

2. Beta-(3-isopropyl-cyclohexyl)-butyraldehyde.

3. A compound of claim 1, wherein $R_1$, $R_2$, $R_3$, and $R_4$ are hydrogen.

4. A compound of claim 1, wherein $R_1$, $R_2$, and $R_3$ are hydrogen, and wherein $R_4$ is methyl.

5. A compound of claim 1, wherein $R_1$ and $R_2$ are methyl, and wherein $R_3$ and $R_4$ are hydrogen.

6. A compound of claim 1, wherein $R_1$ and $R_2$ are hydrogen, and wherein $R_3$ and $R_4$ are methyl.

7. A compound of claim 1, wherein $R_1$, $R_2$, $R_3$, and $R_4$ are methyl.

8. A method of improving, enhancing, or modifying a fragrance formulation through the addition of an olfactory acceptable amount of a compound

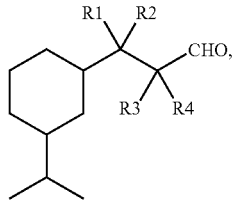

wherein $R_1$, $R_2$, $R_3$, and $R_4$ is independently hydrogen and methyl.

9. A method of claim 8, wherein the compound is beta-(3-isopropyl-cyclohexyl)-butyraldehyde.

10. The method of claim 8 wherein the fragrance is incorporated into a product selected from a perfume, a cologne, a toilet water, a cosmetic product, a personal care product, a fabric care product, a cleaning product, and an air freshener.

11. The method of claim 10 wherein the cleaning product is selected from the group consisting of a detergent, a dishwashing composition, a scrubbing compound, and a window cleaner.

12. The method of claim 8, wherein the amount of the compound added into the fragrance formulation is from about 0.005 to about 10 weight percent.

13. The method of claim 8, wherein the amount of the compound added into the fragrance formulation is from about 0.1 to about 8 weight percent.

14. The method of claim 8, wherein the amount of the compound added into the fragrance formulation is from about 0.5 to about 5 weight percent.

15. A fragrance formulation containing an olfactory effective amount of a compound

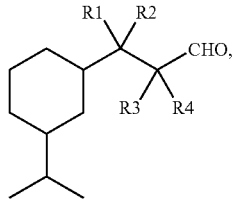

wherein $R_1$, $R_2$, $R_3$, and $R_4$ is independently hydrogen and methyl.

16. A fragrance formulation of claim 15, wherein the compound is beta-(3-isopropyl-cyclohexyl)-butyraldehyde.

* * * * *